United States Patent [19]

Miller et al.

[11] Patent Number: 5,801,159
[45] Date of Patent: Sep. 1, 1998

[54] METHOD AND COMPOSITION FOR INHIBITING CELLULAR IRREVERSIBLE CHANGES DUE TO STRESS

[75] Inventors: Guy Miller, Mountain View; Lillian Lou, Palo Alto; John Nakamura, San Jose, all of Calif.

[73] Assignee: Galileo Laboratories, Inc., Sunnyvale, Calif.

[21] Appl. No.: 607,022

[22] Filed: Feb. 23, 1996

[51] Int. Cl.⁶ .................................................. A61K 31/70
[52] U.S. Cl. .................... 514/45; 514/46; 514/47; 514/48; 536/26.7; 536/27.6; 536/27.8; 536/27.81
[58] Field of Search .................... 536/26.7, 27.6, 536/27.8, 27.81; 514/45, 46, 47, 48

[56] References Cited

U.S. PATENT DOCUMENTS

| | | | |
|---|---|---|---|
| 4,575,498 | 3/1986 | Holmes et al. | 514/43 |
| 5,066,578 | 11/1991 | Wikman-Coffelt | 435/1 |
| 5,145,771 | 9/1992 | LeMasters et al. | 435/1 |
| 5,320,846 | 6/1994 | Bistrian et al. | 424/439 |
| 5,405,742 | 4/1995 | Taylor | 435/1 |
| 5,514,536 | 5/1996 | Taylor | 435/1.2 |
| 5,565,317 | 10/1996 | Dohi et al. | 435/1.2 |

OTHER PUBLICATIONS

Gao et al., "Evidence that Adenosine Is a Key Component in Carolina Rinse Responsible for Reducing Graft Failure After Orthotopic Liver Transplantation in the Rat," *Transplantation*, 52(6), 992–998 (Dec. 1991).

Marsh et al.(I), "Hypothermic Preservation of Hepatocytes. III. Effects of Resuspension Media on Viability After Up To 7 Days of Storage," *Hepatology*, 13(3), 500–508 (1991).

Marsh et al. (II), "Glycine Prevention of Cold Ischemic Injury in Isolated Hepatocytes," *Cryobiology*, 28, 105–109 (1991).

Weinberg et al.(I), "Amino Acid Protection of Cultured Kidney Tubule Cells Against Calcium Ionophore–Induced Lethal Cell Injury," *Laboratory Investigation*, 65(6), 671–678 (1991).

Weinberg et al.(II), "Metabolic Aspects of Protection by Glycine Against Hypoxic Injury to Isolated Promixal Tubules," *J. Am. Soc. Nephrology*, 1(7), 949–958 (1991).

*Primary Examiner*—John Kight
*Assistant Examiner*—L. Eric Crane
*Attorney, Agent, or Firm*—Flehr Hohbach Test Albritton & Herbert LLP

[57] ABSTRACT

Purine derivatives are provided for treatment of cellular stress, particularly hypoxia. By administering the purine derivatives by themselves or in conjunction with other compounds, particularly electron acceptor compounds and/or amino acids, the time for irreversible cellular changes, particularly mortality, can be greatly extended.

20 Claims, 14 Drawing Sheets

METHOD AND COMPOSITION FOR INHIBITING CELLULAR IRREVERSIBLE CHANGES DUE TO STRESS

BACKGROUND

There are many effectors of cell stress. These include infection, thermal, cryogenic, osmotic, hyper- and hypogravity, transplantation, starvation, growth in various reactors, such as bio reactors, fermentation, food preparation, etc., toxicity, such as inhalation of various toxic gases, e.g. HCN, phosphates, thiophosphates, etc., drug overdoses, and the like. The particular mechanism by which cells respond to stress, become quiescent, and try to protect themselves from irreversible injury is not well understood. It may involve one or more different mechanisms.

Of particular interest is hypoxia or ischemia. Cells require energy to live and carry out their given tasks. For many important cells in our body, oxygen is a necessary ingredient to produce cell energy. The cell combines products from the foods we eat with the oxygen we breathe to produce cell energy. This energy powers the cell and sustains life. Without the proper amount of energy, the cell fails to work and if the inadequate energy level is maintained for a period of time during which the cell cannot maintain it's viable state, the cell will die. For tissues that are carrying out many energy consuming activities, such as the brain and heart, the absence of oxygen can result in cell death in as little as 7–15 minutes. Cells are always at work, producing energy to sustain life. When this process is disrupted, even for brief periods of time, death to a vital body part can result with death to the host. When inadequate amounts of oxygen are available to maintain normal function, the cell is said to be hypoxic or experiencing hypoxia.

One may distinguish between metabolic hypoxia and bioenergetic hypoxia. These are distinguished between altered bioenergetic functions due to insufficient oxygen supply to mitochondrial cytochrome oxidase ("bioenergetic hypoxia") and altered metabolic functions due to insufficient oxygen supply to other enzymes that require molecular oxygen as substrate ("metabolic hypoxia"). There is no agreement today as to the specific mechanisms associated with irreversible injury to cells during an extended oxygen starvation.

Because of the diverse conditions under which cells are stressed, both in vitro and in vivo, where one wishes to maintain their viability, there is substantial interest in developing methods and compositions which will improve the outcome for the cells, in the event of oxygen starvation. There is, therefore, substantial interest in providing improved methods for reducing the probability of irreversible damage to cells during a limited period of stress, so as to allow the cells to have a higher probability of recovery upon removal of the stress condition.

General information concerning metabolic stress may be found in Atkinson, Cellular energy metabolism and its regulation, 1977, Academic Press, NY; Hochachka et al., Surviving hypoxia: mechanisms of control and adaptation, 1993, CRC Press, Inc., FL; and Alberts et al., Molecular biology of the cell, 1994, Garland Publishing, Inc., NY.

SUMMARY OF THE INVENTION

Methods and compositions are provided for enhancing cellular resistance to irreversible changes in cellular function, including mortality, due to stress. The stress might take any form, particularly lack of oxygen. The stress is relieved by adding compounds to the cells, which compounds are added individually or in combination and include purines, purine nucleosides and derivatives thereof, electron acceptors, amino acids, and particular individual compounds, in an amount sufficient to inhibit irreversible changes in cellular function, particularly leading to mortality. Combinations may be mixtures or covalently bonded combinations, particularly esters. The compositions find use in storing cells, tissues and organs, in fermentation and in the treatment of hosts under stress.

DESCRIPTION OF THE SPECIFIC EMBODIMENTS

Figure 1:
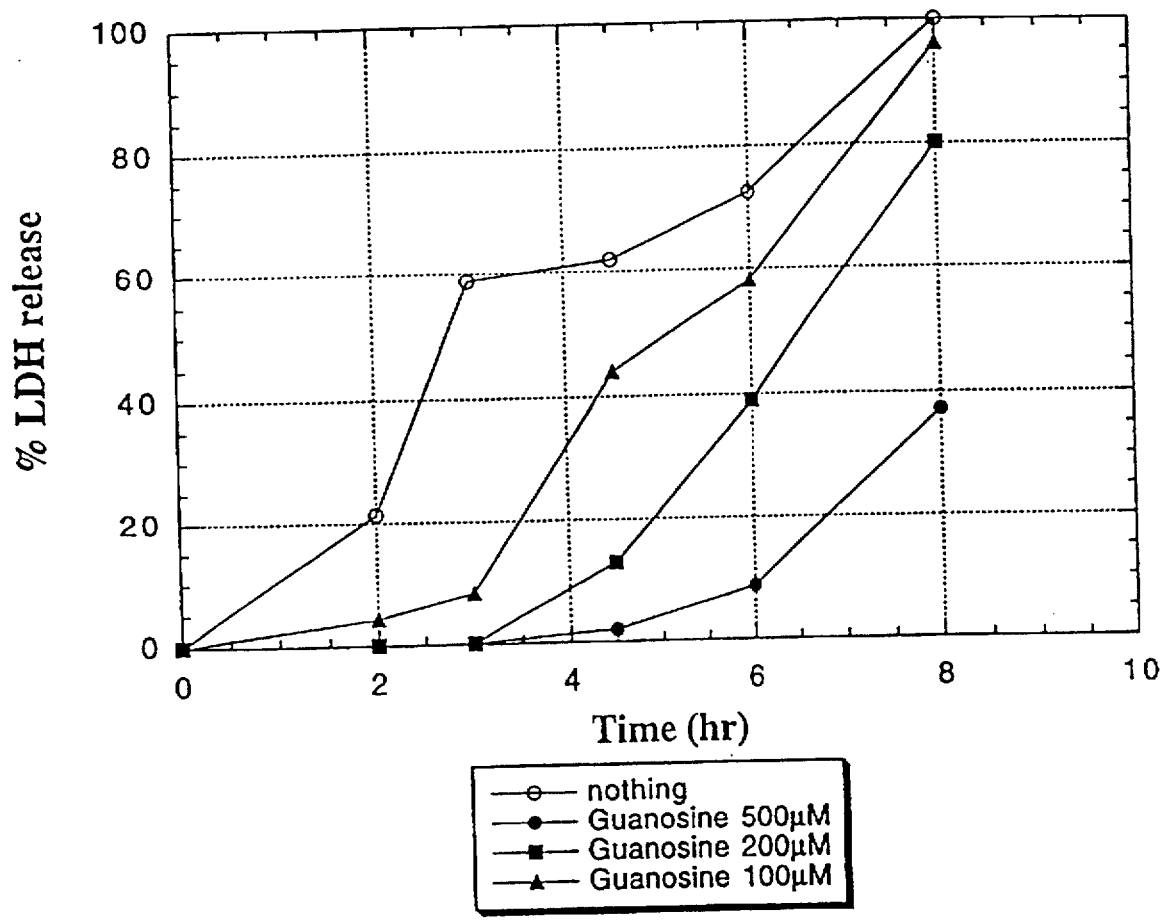
FIG. 1 is a graph depicting percentage of LDH release over time wherein ○ denotes nothing, ● denotes 500 μM guanosine, ■ denotes 200 μM guanosine, and ▲ denotes 100 μM guanosine.
Figure 2:
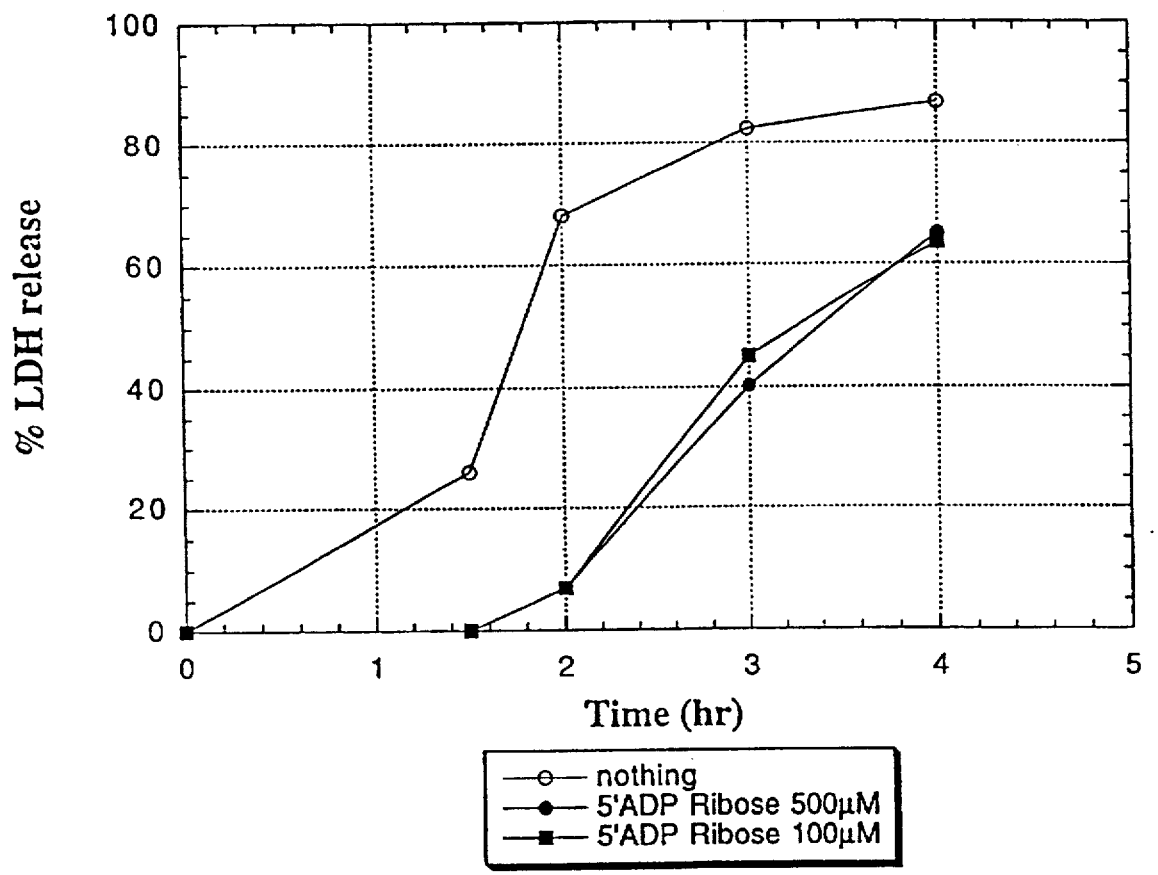
FIG. 2 is a graph depicting percentage of LDH release over time wherein ○ denotes nothing, ● denotes 500 μM 5'ADP and ■ denotes 100 μM 5'ADP.
Figure 3:
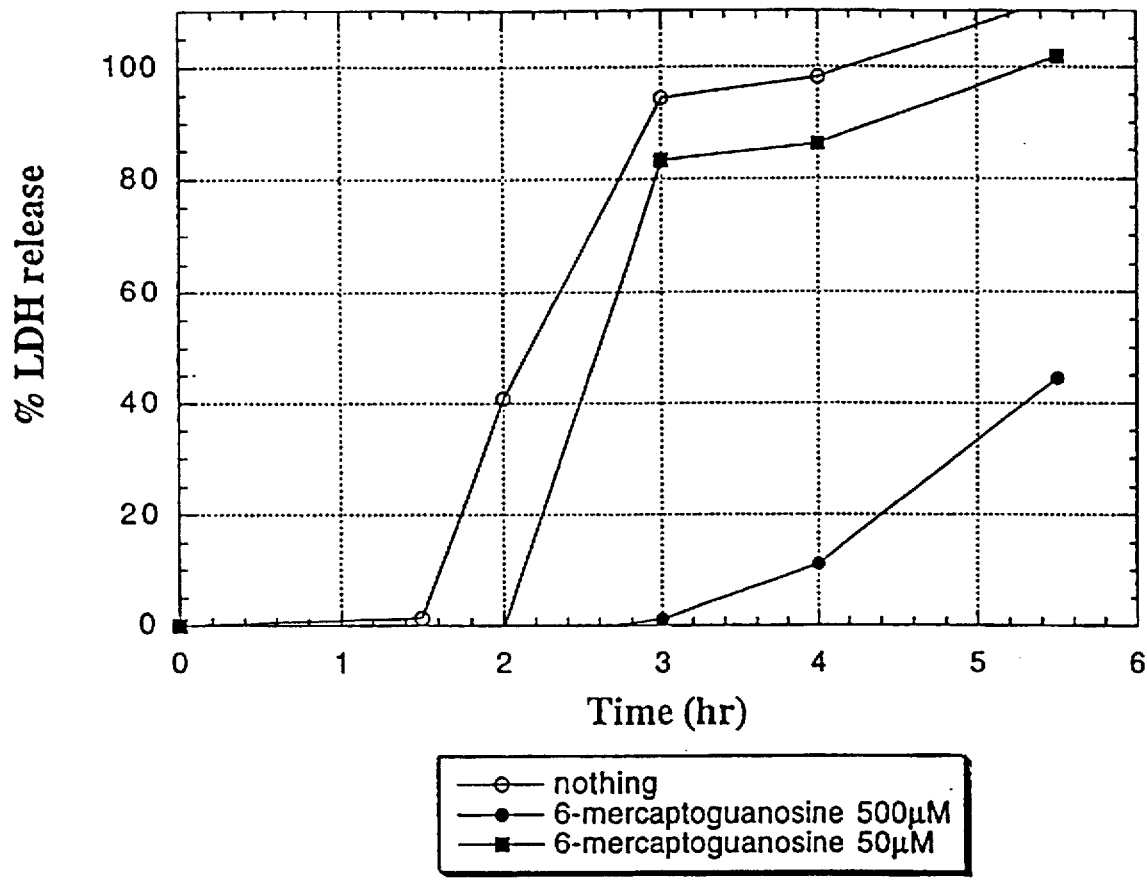
FIG. 3 is a graph depicting percentage of LDH release over time wherein ○ denotes nothing, ● denotes 500 μM 6-mercaptoguanosine and ■ denotes 50 μM 6-mercaptoguanosine.
Figure 4:
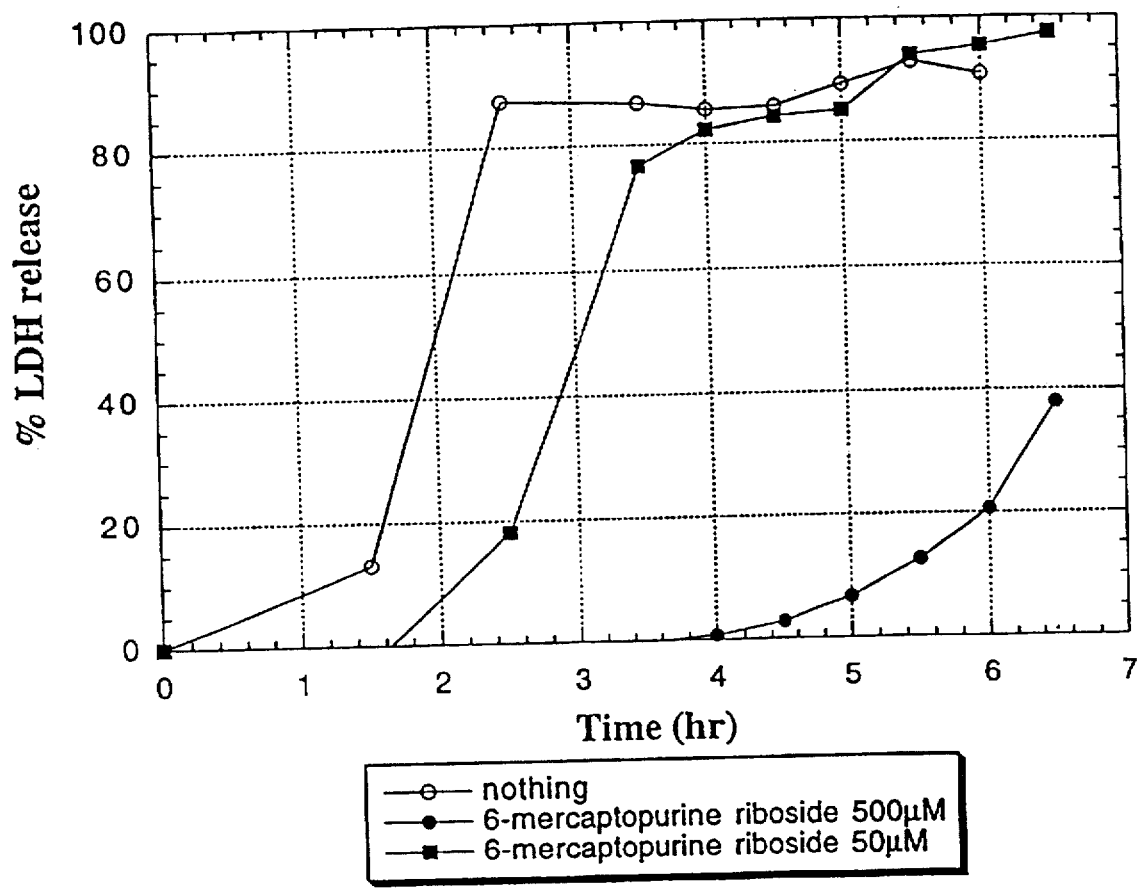
FIG. 4 is a graph depicting percentage of LDH release over time wherein ○ denotes nothing, ● denotes 500 μM 6-mercaptopurine and ■ denotes 50 μM 6-mercaptopurine.
Figure 5:
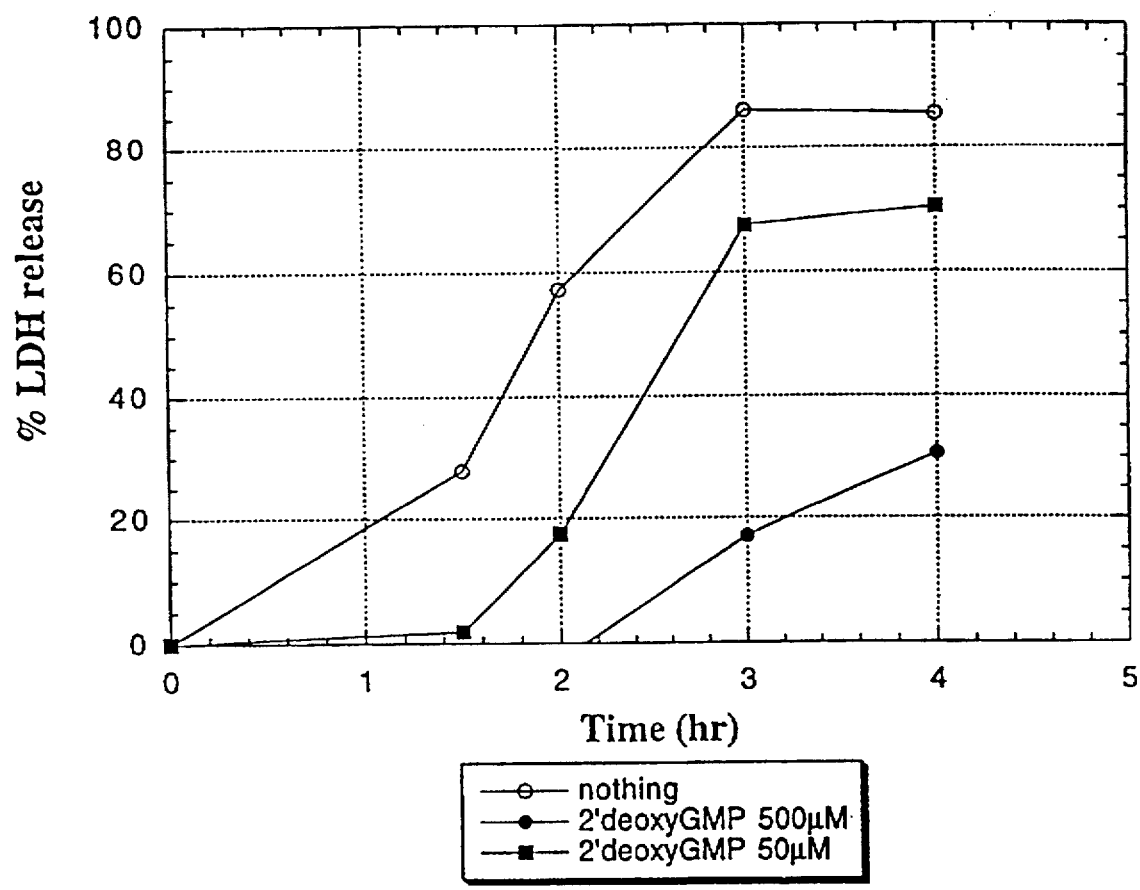
FIG. 5 is a graph depicting percentage of LDH release over time wherein ○ denotes nothing, ● denotes 500 μM 2'deoxyGMP and ■ denotes 50 μM 2'deoxyGMP.
Figure 6:
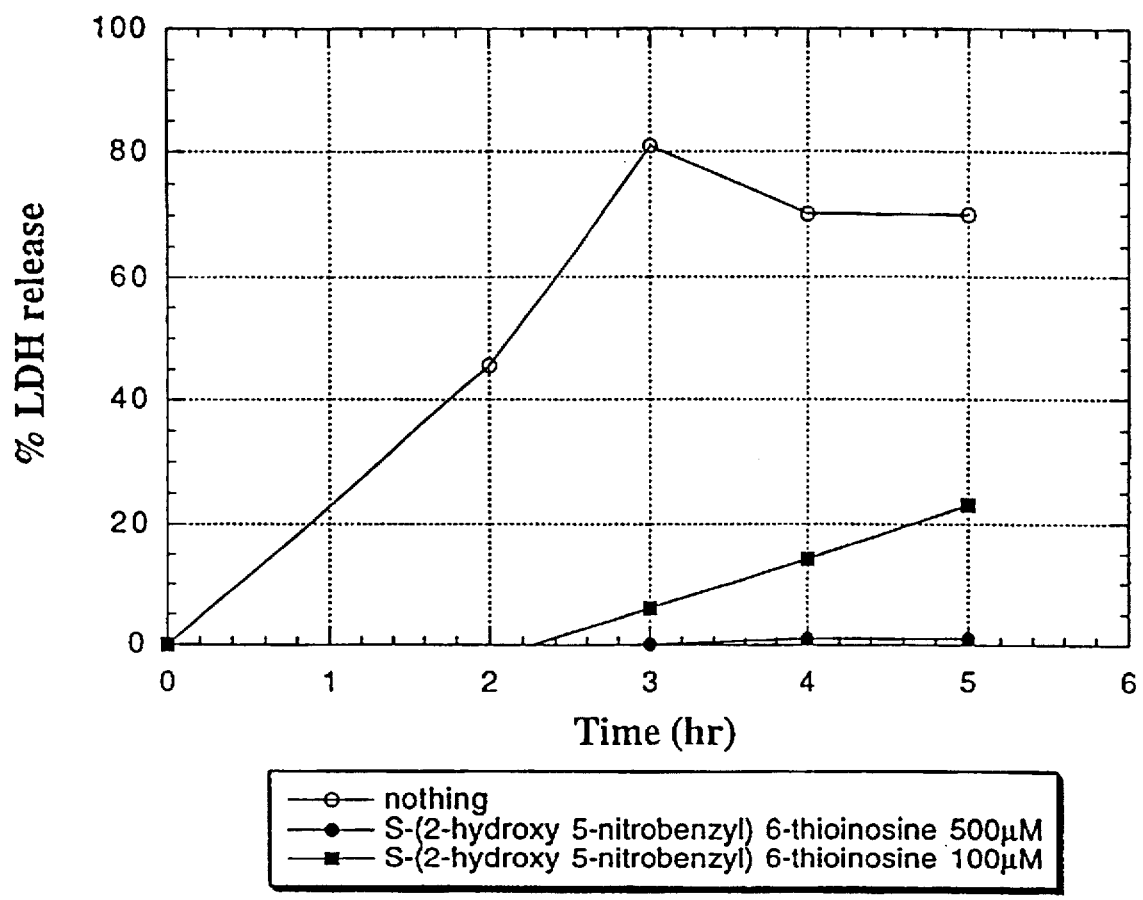
FIG. 6 is a graph depicting percentage of LDH release over time wherein ○ denotes nothing, ● denotes 500 μM S-(2-hydroxy 5-nitrobenzyl) 6-thioinosine and ■ denotes 100 μM S-(2-hydroxy 5-nitrobenzyl) 6-thioinosine.
Figure 7:
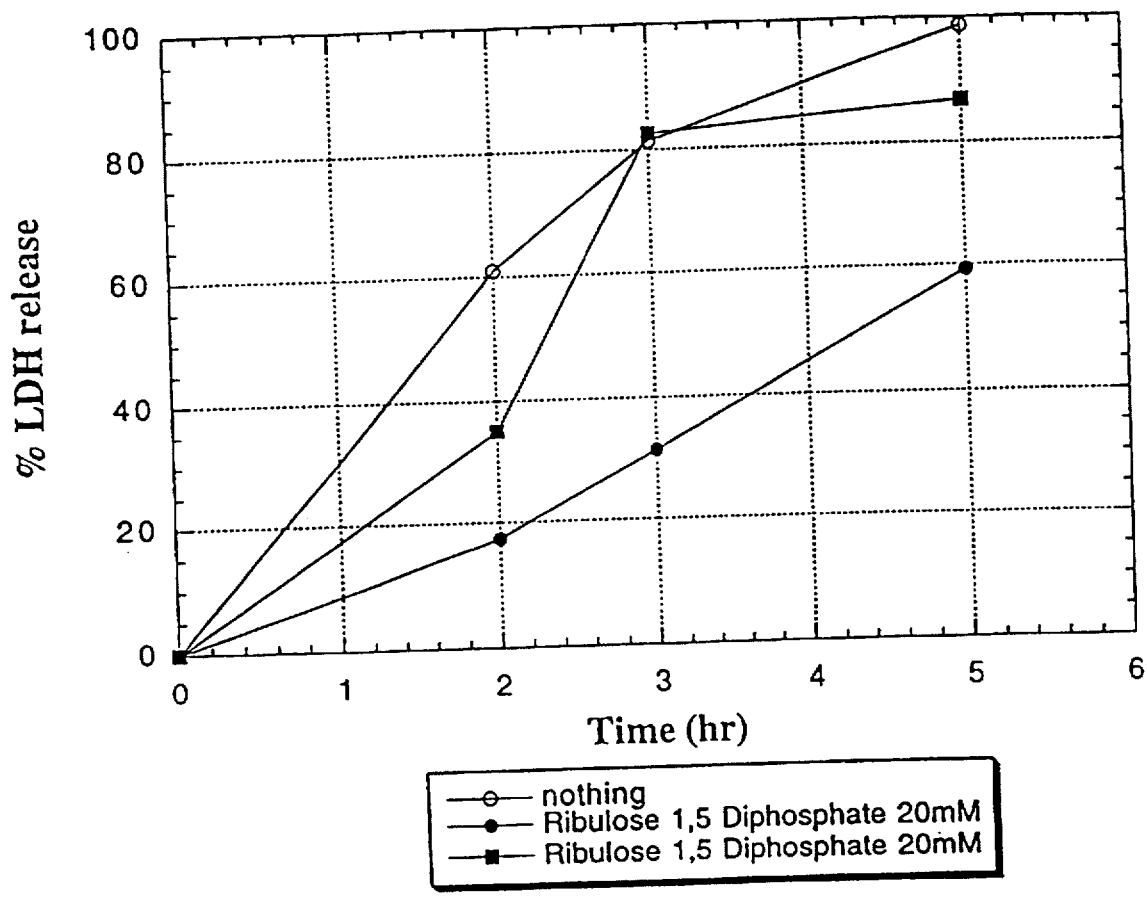
FIG. 7 is a graph depicting percentage of LDH release over time wherein ○ denotes nothing, ● denotes 20 μM ribulose 1,5 diphosphate and ■ denotes 20 μM ribulose 1,5 diphosphate.
Figure 8:
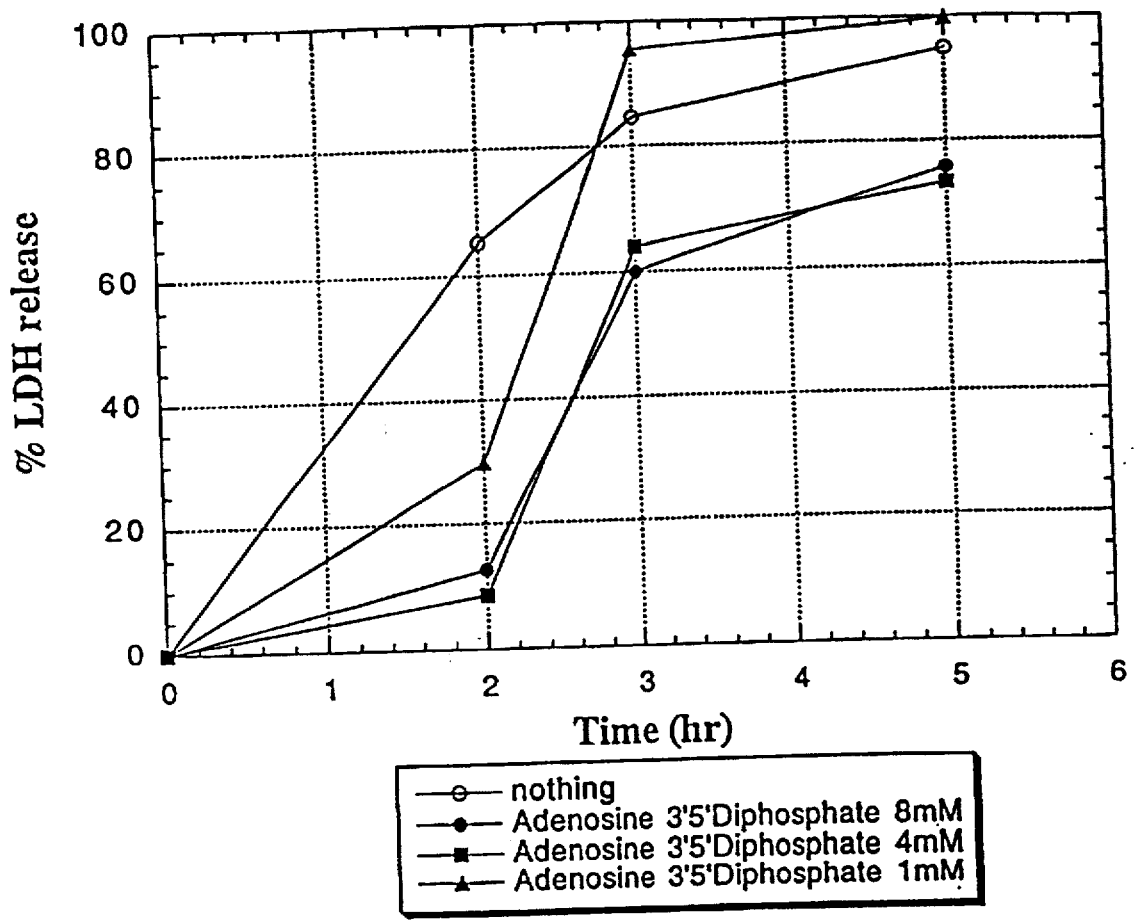
FIG. 8 is a graph depicting percentage of LDH release over time wherein ○ denotes nothing, ● denotes 8 mM adenosine 3'5'diphosphate, ■ denotes 4 mM adenosine 3'5'diphosphate, and ▲ denotes 1 mM adenosine 3'5'diphosphate.
Figure 9:
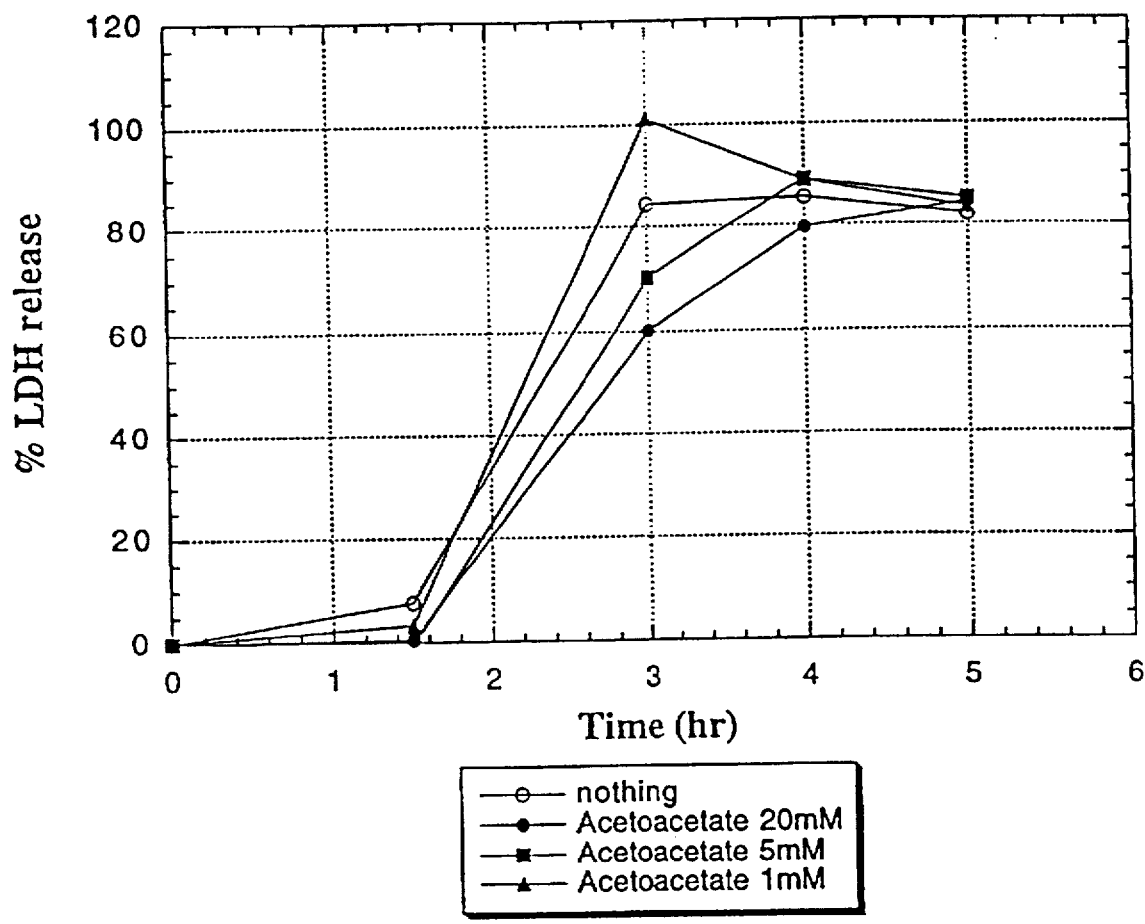
FIG. 9 is a graph depicting percentage of LDH release over time wherein ○ denotes nothing, ● denotes 20 mM acetoacetate, ■ denotes 5 mM acetoacetate, and ▲ denotes 1 mM acetoacetate.
Figure 10:
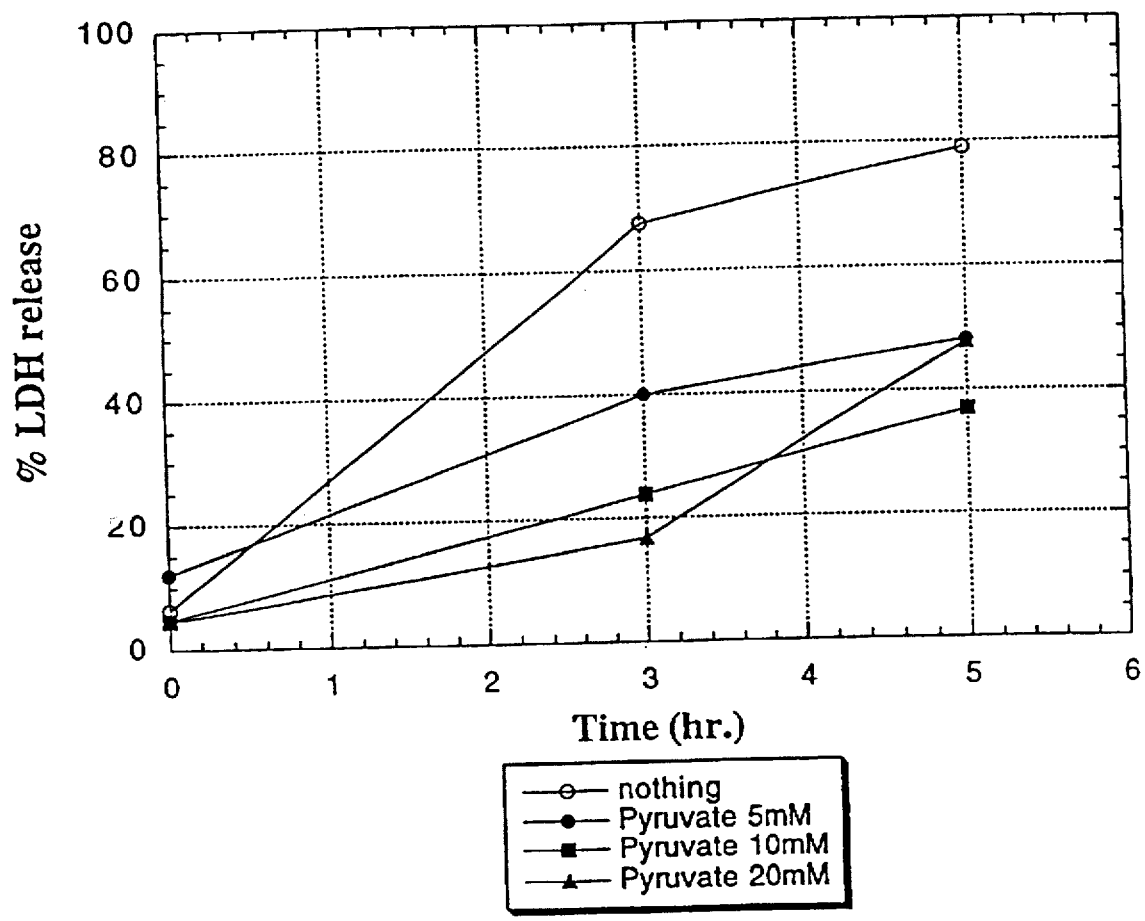
FIG. 10 is a graph depicting percentage of LDH release over time wherein ○ denotes nothing, ● denotes 5 mM pyruvate, ■ denotes 10 mM pyruvate, and ▲ denotes 20 mM pyruvate.
Figure 11:
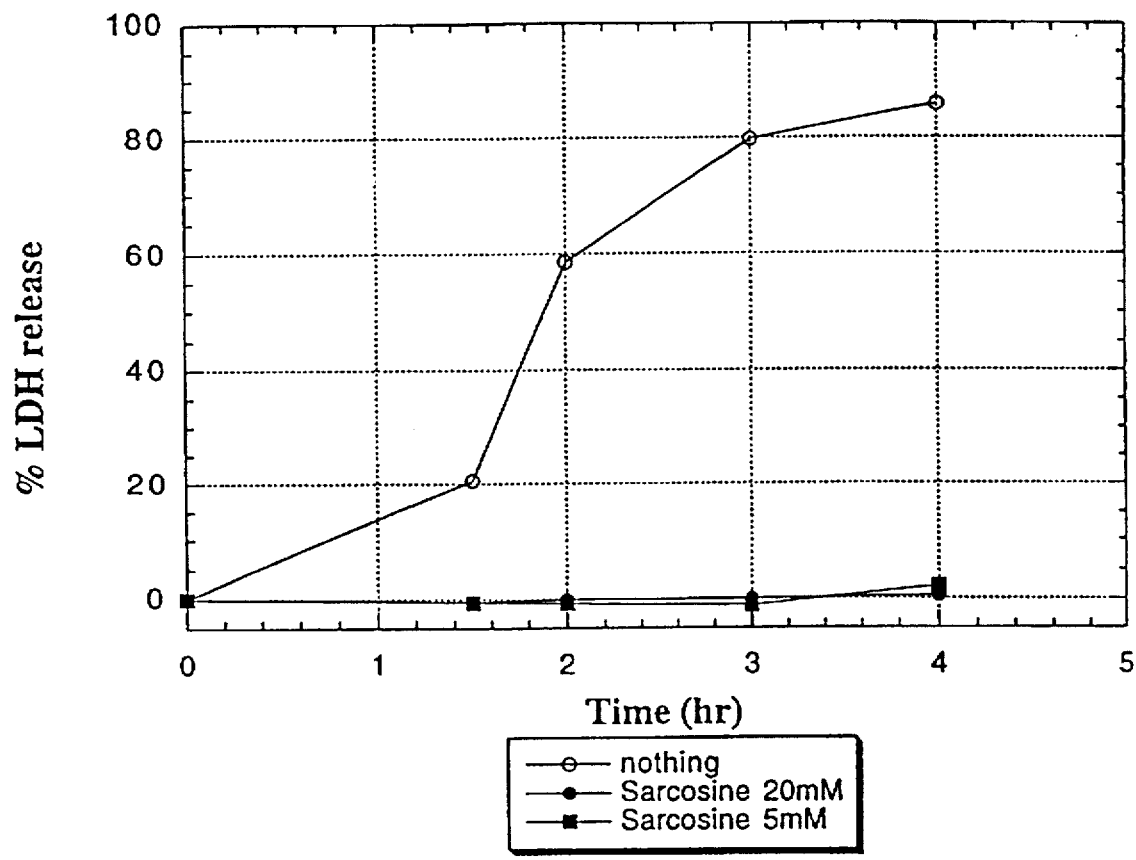
FIG. 11 is a graph depicting percentage of LDH release over time wherein ○ denotes nothing, ● denotes 20 mM sarcosine and ■ denotes 5 mM sarcosine.
Figure 12:
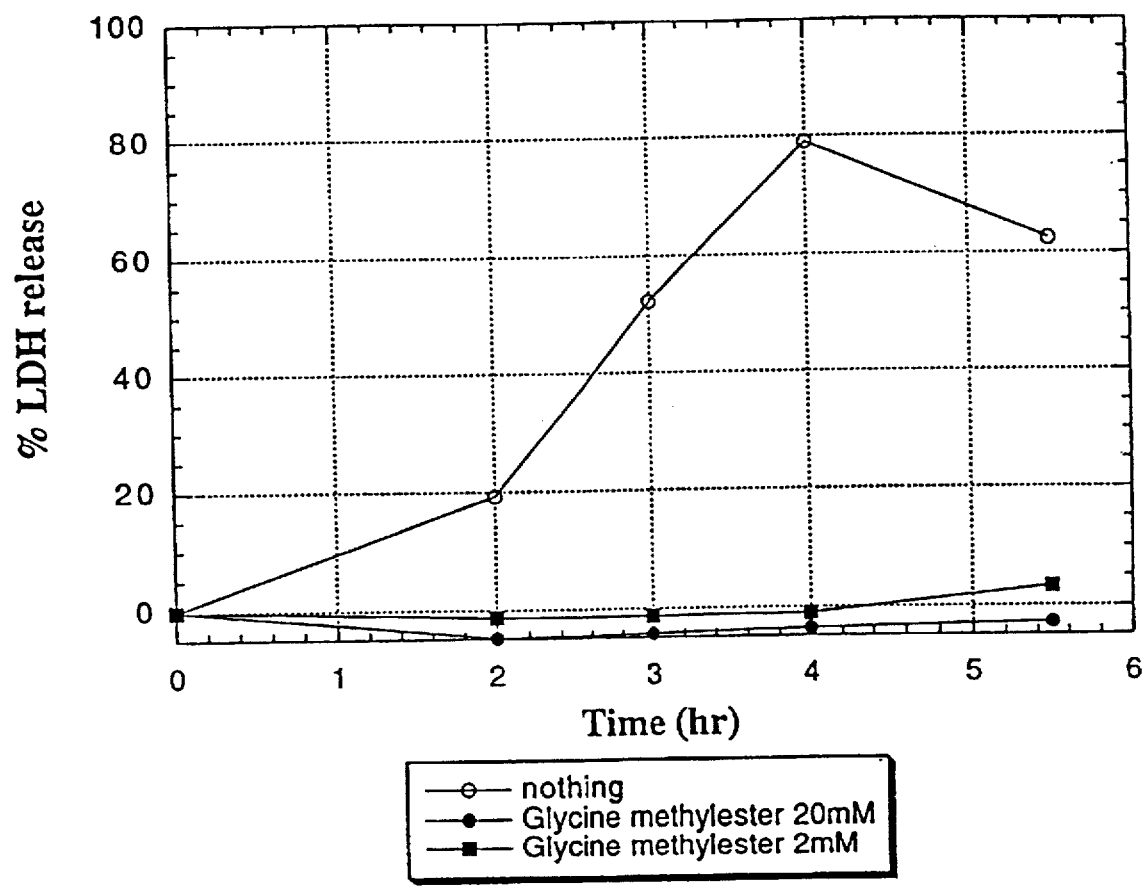
FIG. 12 is a graph depicting percentage of LDH release over time wherein ○ denotes nothing, ● denotes 20 mM glycine methylester and ■ denotes 2 mM glycine methylester.
Figure 13:
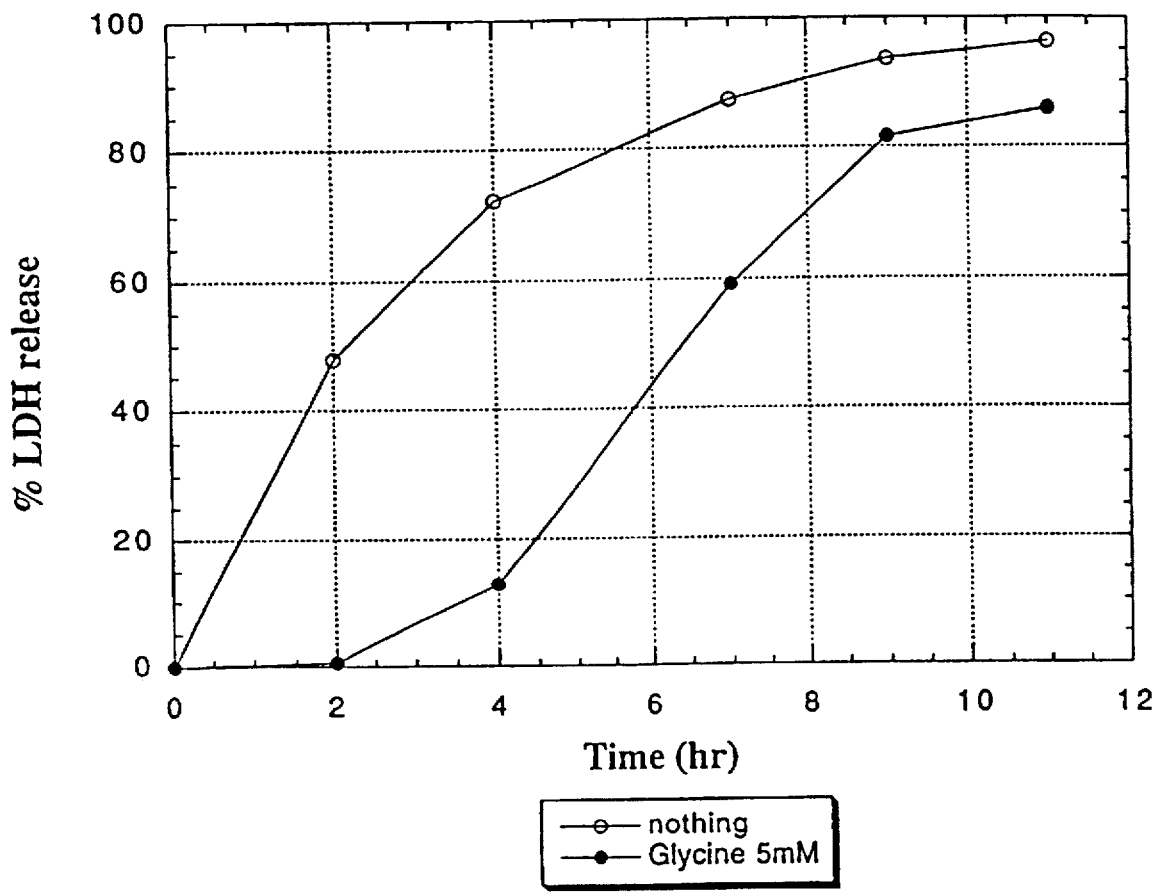
FIG. 13 is a graph depicting percentage of LDH release over time wherein ○ denotes nothing and ● denotes 5 mM glycine.
Figure 14:
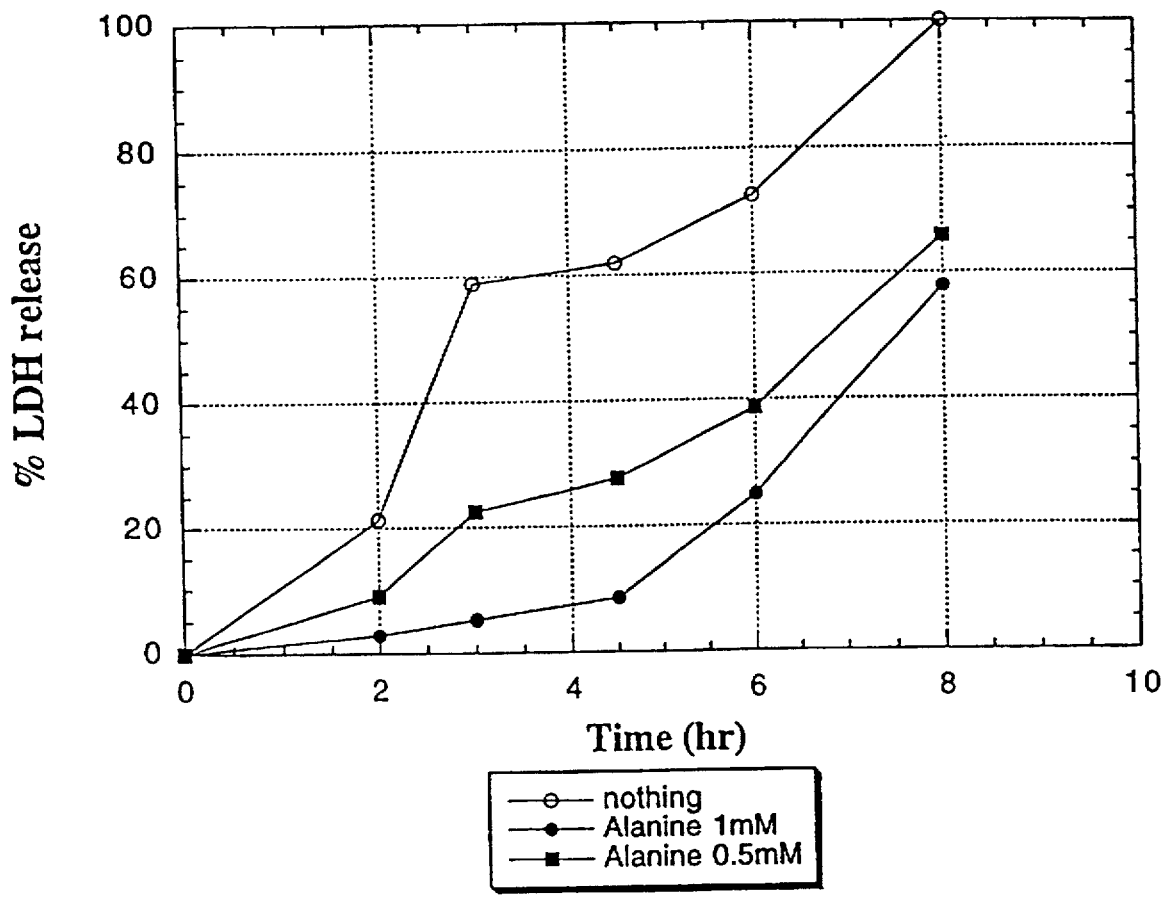
FIG. 14 is a graph depicting percentage of LDH release over time wherein ○ denotes nothing, ● denotes 1 mM alanine and ■ denotes 0.5 mM alanine.

Treatments of stress are provided involving individual or combinations of compounds which serve to enhance mammalian cellular resistance to irreversible changes in cellular function. The stress may take any form, but a particular interest is hypoxia. The stress may be a result of a wide variety of conditions, as described above, both in vitro and in vivo. The time of onset of irreversible changes, as may be evidenced by cellular release of lactate dehydrogenase (LDH) into the extra- cellular medium or formation of lactate, or cellular mortality may be greatly extended. Depending upon the particular environment in which the subject compositions are employed, the compositions may be added to an extracellular medium, administered to a host orally or parenterally, or by other convenient means.

Mammalian cells can be subjected to stress in a wide variety of environments. When growing cells, carrying out fermentation, using cells for production of various products, performing cellular modifications of substrates, and the like, cells may be subjected to stress. A particular problem is the inability to maintain a sufficient oxygen level in the medium, so that some portion of the cells will from time to time be oxygen starved. This can result in the loss of yields of a desired product, the release of cellular contents, which can interfere with the isolation and purification of product, clogging of pores of cellular reactors, and the like.

In ex vivo situations, where one wishes to store cells, there is great interest in maintaining the viability of the cells. This occurs in organ transplantation, cryogenic preservation of cells and tissue, and the like. The cells or organ may be maintained in a medium comprising the subject compositions during storage. Prior to introducing the stress, such as freezing, one may combine the cells with the protective composition to inhibit stress during the freezing, storage, and restoration. Thus, the cells, tissue or organ may be combined with the appropriate medium containing the subject compositions and then treated in accordance with conventional conditions.

There are also numerous situations in vivo, where one is concerned with stress. The subject methods may be used for prevention before the onset of hypoxia. The situations include elective revascularization, such as surgical ischemia, transplantation, carotid endarterectomy, and surgical hypoperfusion. Specific situations involving surgical ischemia include surgery while supported by cardio-pulmonary bypass, aortic surgery which includes abdominal aortic aneurysm, supra- renal or infra-renal, thoraco-abdominal aneurysm repair, aortic arch repair, particularly as in circulatory arrest. In the case of transplantation, it may involve solid organs, such as the kidney, liver, lung, heart, skin, or the like, or dispersed cells, such as bone marrow, stem cells, or hematopoietic cells.

One may use the subject compositions to prevent injury prior to the onset of hypoxia. This may involve carotid endarterectomy, renal artery stenosis, mesenteric ischemia (bowel angina), thoracic surgery, airway surgery-apnea, peripheral revascularization, thermal-palatal grafting. Surgical hypoperfusion may involve elective hypotension with anticipated blood loss, cranial facial surgery and oncologic indications. In many situations, one may use the subject compositions for rescue, which involves the use of the compositions after onset of hypoxia. This may involve non-elective revascularization, such as in the case of stroke or myocardial infarction, hemorrhagic shock, trauma, head injury, spinal cord injury or shock, severe burn and cadaveric organ harvest.

Other situations in which the subject compositions may find application include acute respiratory distress syndrome (ARDS), fetal distress, multisystem organ dysfunction, sepsis and sepsis syndrome, toxicities such as inhalation and injury, poisonings, particularly involving compounds binding to metal atoms such as cyanide and carbon monoxide, extracorporeal membrane oxygenation (ECMO), and systemic wasting, as in the case of cancer and AIDS.

The subject compositions which are of particular interest are physiologically acceptable purine derivatives, particularly purine ribosides which serve to extend the time for onset of irreversible changes in the cellular host, particularly changes leading to mortality. The purines have the following formula:

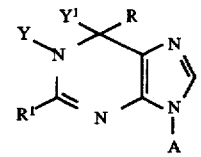

wherein:

A is a sugar or a phosphorylated sugar, particularly ribose, deoxyribose, and phosphorylated derivatives thereof, particularly 3' and/or 5'-phosphate and 5'-pyrophosphate, including derivatized phosphates, such as phosphate esters and anhydrides, particularly mixed anhydrides, where the esters may be alkyl esters of alkyl groups of from 1 to 3 carbon atoms or of sugars, e.g. ribose, deoxyribose and phosphorylated esters thereof, such as 3' and 5'-esters, and the mixed anhydrides may be anhydrides with carboxylic acids, such as pyruvate, and combinations thereof, e.g. ADP-r-r-P-r-P, where r is ribosyl and P is phosphate, where the final P may be bonded to a nucleoside;

R and $R^1$ may be nitrogen, oxygen or sulfur, where the sulfur may be substituted or unsubstituted, and the remaining valences will be satisfied by hydrogen, and where R amy be taken with $Y^1$ to define a doubly bonded heteroatom;

Y and $Y^1$ are hydrogen or may be taken together to form a double bond between the atoms to which they are bonded or $Y^1$ may be taken together with R to form a double bond to the atom designated by R.

Various compounds coming within the formula are guanosine, adenosine, inosine, 6-mercaptopurine riboside, adenosine diphosphate, adenosine monophosphate, inosine monophosphate, 2'-deoxyadenosine-5'-monophosphate, 2-inosine-5'-monophosphate, 2-deoxyguanosine-5'-monophosphate, S-(2-hydroxy-5-nitrobenzyl)-6-thioinosine, erythro-9-(2-hydroxy-3-nonyl) adenine and S-4-nitrobenzyl-6-thioinosine.

Various physiologically acceptable electron acceptors may be used in conjunction with the subject compositions. These electron acceptors may take any one of several structures and functionalities, such as oxo, aromatic heterocycles, transitional metal complexes and enzymes, as well as combinations thereof. These electron acceptors include ketones, particularly α- and β-ketocarboxylic acids, such as pyruvate, oxaloacetate, acetoacetate, and menadione; other types of compounds, such as protoporphyrins, ascorbate, nicotinamide mononucleotide (oxidized or reduced), FMNH, glutathione (oxidized or reduced), superoxide dismutase, with various metal cofactors such as Mn, Mg, and Cu, deferoxamine, bathocuprine, allopurinol, N-acetyl cysteine, and the like. These compounds find particular use either in combination with the compounds indicated above or by forming the ester of the sugar modified purine, so as to form a single compound which is readily hydrolyzable under physiologic conditions.

Various amino acids, individually or as oligopeptides, particularly dipeptides, may find application in association with the subject purines. These amino acids include both natural and unnatural amino acids, and their derivatives, particularly their alkyl esters of from 1–2 carbon atoms and their amides. The amino acids will for the most part be aliphatic, but may include aromatic acids. Amino acids which may find use include glycine, N,N-dimethylglycine, glycine amide, glycine methyl ester, alanine, alanine methyl ester, serine, glutamate, glutamine, lysine, arginine, sarcosine, serine, tryptophan, glycyl glycine, glycyl alanine, alanyl alanine, etc.

Other compounds of interest include various sugars and their phosphorylated derivatives, such as ribulose, 1,5-diphosphate, fructose, 1,6-diphosphate, fructose, glucose, fructose-6-phosphate, and mannose.

Finally, additional compounds of interest include phosphoglycerates, where the phospho group at the 3 position is esterified with alkyl groups of from 1–2 carbon atoms and/or the 2-hydroxyl group is esterified with pyruvate.

Of particular interest are combinations of the purine derivatives and at least one additional active physiologically acceptable component, particularly an electron acceptor, more particularly a ketone electron acceptor, e.g. pyruvate, an amino acid or derivative thereof, particularly an amino acid of from 2–3 carbon atoms, more particularly glycine, where the amino acid may have C- and N-alkyl substituents of from 1 to 2 carbon atoms, particularly methyl. Particularly, where the individual compounds are charged, to enhance cellular absorption and transport, when possible the two compounds may be reacted to reduce the total charge, as in the case of an alcohol and an acid to produce an ester. The bonds which are formed will usually be physiologically labile, such as esters, e.g. phosphate and carboxylate, amides, anhydrides, and the like. Generally, the molar ratio of the other components to the purine will be in the range of about 1:0.5–100, more usually 1:1–50 since the additional materials will generally be safe at high concentrations, one may conveniently use relatively high ratios of the adjunctive materials to the purine and then reduce the concentrations to determine the optimum concentration.

For the most part, the subject compounds are physiologically safe up to relatively high concentrations. Formulations of the subject compositions may be prepared as concentrates for dilution prior to use. The amount of a subject compound which will be administered will be dependant upon the safety level of the compound, the context in which it is used, the manner of administration, whether localized or systemic, whether oral or parenteral, the particular indication, the frequency of administration, whether as a bolus, continuous, e.g. intravenous, or the like, or other conventional considerations. Generally, concentrations of the purine compounds as the primary compound will vary from about 0.1 μm to 50 μM, more usually from about 10 μm to 1 mM. Where combinations are used, frequently the concentration of the primary compound will be in the lower portion of the range, generally being 1 mM or less.

For in vitro or ex vivo administration, the compounds may be provided in the medium, as a single bolus, by repetitive addition, by continual infusion, or the like. During the course of the treatment, the concentration of the subject compositions may be monitored to insure that the desired level is maintained. For in vivo administration, where the administration is oral, the subject compositions may be provided as tablets, capsules, powders, solutions, dispersions, or the like. For rectal administration, the subject compositions may be provided as suppositories, as solutions for enemas, or other convenient application. Otherwise, the subject compositions may be administered intravascularly, arterially or venous, subcutaneously, intraperitoneally, intraorgan, intramuscularly, or the like.

For oral administration, the subject compositions may be compounded with other physiologically acceptable materials which can be ingested, such as in foods, e.g. food bars, beverages, powders, food additives, candies and the like To determine the optimum concentration for any application, conventional techniques may be employed. Thus, for in vitro and ex vivo use, a variety of concentrations may be used and various assays employed to determine the degree of dysfunction of the cells when exposed to stress, particularly hypoxia. One technique which may be employed for mammalian cells, is the extra- and intracellular distribution of lactate dehydrogenase over time. The longer the period that the intracellular lactate dehydrogenase is maintained as against the proportion in the extracellular medium, the better the cells are protected from irreversible changes leading to mortality. Conveniently, the lactate dehydrogenase assay described in the experimental section may be employed. Alternatively or in conjunction with the lactate dehydrogenase assay, one may also look for the formation of lactate. The greater the formation of lactate, the greater the preservation of the cells.

For preservation of cells, the subject compositions may be added for a short time, usually at least about 0.5 hour and then removed, maintained for long periods of time with the cells, including weeks or months or longer, may be replenished periodically, or the like. Since the subject compounds are for the most part safe, without significant side effects, the subject compounds may be maintained for the entire stress period or for an extended period in anticipation of stress.

In a number of situations there may be oxygen deprivation or other stress due to physical activity, such as exercise, or sports activities, or surgery, or the like. The subject compositions may be formulated as foods, either solid or liquid, such as food bars, cereals, cooked foods, beverages, or the like. Usually, the amount of the active ingredient will be at least 0.1 g per serving, and may be 0.5 g per serving or more, generally no exceeding about 5 g, more usually not exceeding about 2 g per serving. The subject compositions may combined with particular foods to enhance their effectiveness, such as high protein foods, foods which enhance transport across the gut, such as gums, foods which provide for compatible energy sources, and the like.

The following examples are offered by way of illustration and not by way of limitation.

EXPERIMENTAL

Generalized Protocol for Assaying Protection

I. Protocol for harvesting and assaying Wif B cells for LDH release with various compounds A. Plating cells onto coverslips 1. Autoclave glass coverslips 18 mm diam. (VWR). Insert 9 sterile coverslips into a petri dish and arrange in 3 rows of 3. Adhere the coverslips to the petri dish by flaming tweezers and melting plastic over coverslips in 4 or more places around each coverslip.

2. From a culture flask (T75), check cell density. Cells should not be confluent, they should appear in clumps or in log phase growth.

3. Aspirate off media. Add 25 ml PBS to bottom of flask and do not disturb adherent cells. Tilt flask to gently wash adherent cells and aspirate.

4. Add 2 ml of prepared trypsin solution to bottom and gently overlay solution to adherent cells. Let stand for 3 minutes. Tap flask fairly vigorously to dislodge adherent cells from surface. Add 8 ml of Wif B media with serum over any remaining adherent cells and mix gently to get cell suspension.
   a. For Wif B media, serum, and trypsin solution components and protocols, see below.
5. From suspension, determine cell density. Each petri dish is 60 cm$^2$ and the desired density is 20,000 cells/cm$^2$ for 1.2 million cells per dish. Make volume up to 15 mL of total media to add to each petri dish.
6. The next day transfer coverslips to 6 well plates with 5 ml of Wif B media in each well. Change media every other day until the 7th day. Change media every day until cells are used. Cells will be used between 9 and 11 days in culture starting from the day cells were plated onto coverslips. 10 days in culture is optimum.

B. Assaying Wif B cells for LDH release
1. On the day of the assay, remove media from wells and wash cells with 1×5 ml each well Balanced Salt solution (below). pH 7.4 total mOsm=288: Balanced Salt solution contains: 1.3 mM CaCl2, 1.2 mM MgCl2, 5 mM kCl, 25 mM Hepes, 1 mM KH2PO4, 115 mM NaCl.
2. Dilute each compound with respective Balanced Salt solution containing respective amounts of NaCl to make up for osmolarity (refer below for calculation sample). Make serial dilutions in isotonic Balanced Salt solution above. For testing compounds 1 mM or less, dilute in 115 mM HB (above) or make 250 mM (500×) solution in DMSO and insert 10 µl in each well and mix.
3. Incubate compounds (5 ml each well) with cells for half an hour at 37° C. After incubation, swirl gently the six well plates and take 50 µl of sample from each well and insert into 96 well microtiter plate. This is the time 0 (background) point. Add 5 µl 100 mM DNP or 5 µl of 100 µM, antimycin A in DMSO to each well (final concentration 100 µM, 100 nM, respectively). Use 2 pipets to mix gently. Take 50 µl at each time point and insert into 96 well microtiter. Keep microtiter plate at 4° C.
4. At the end of the time course, lyse the remaining cells on the coverslip by adding 10× lysine buffer to remaining media and aspirate vigorously with P1000.
   a. 10× lysing buffer contains: 10% triton-X in 115 mM NaCl HB buffer. This lysate will include amount LDH remaining in the cells+in the media which= total LDH activity.
5. Remove 50 µl at each time point. At the end of each time course, assay for LDH activity using Boehringer Mannheim Kit (notebook 005 pg. 26) except decrease assay volume to 100 µl.
6. Using Sigma Chicken Liver LDH #L6504 as standard, dilute down standards in 115 mM NaCl HB to=400, 200, 100, 50, 25, 12.5, 0 U/l. Assay 50 µl of each as above.

C. Calculations
1. LDH media OD-bkg: raw OD values—115 mM NaCl HB background.
2. LDH (U/l): LDH activity calculated based on standard curve extrapolation. Note that U/l are not based on final concentration of LDH but rather the inserted U/l of standards above. The true final U/l in the cuvette would be the values divided by 2 (50 µl of 100 µl assay).
3. Dilution factor: 50 µl taken per assay will decrease total volume of sample in each well. For example, the dilution factor of zero time point will be 100 (50 µl of 5 ml). The second time point 50 µl will be taken from 4.95 ml or 99 dilution factor, etc.
4. Adjusted LDH (U/l): LDH (U/l) multiplied by dilution factor.
5. LDH-time 0: This is time 0 LDH or initial background release if any subtracted from values during time course to observe DNP or Antimycin A dependent LDH release during the time course. Time 0 LDH values were also subtracted from LDH value from lysate.
6. % LDH release: LDH-time 0 values divided by LDH in Lysate or total LDH activity.
7. % LDH of Time 0: This is to monitor the amount of release at time 0 due to toxicity of compound or possibly other factors. Compounds exhibiting high time 0 background will be tested to see if the compound interferes with the assay or it will be concluded that compound may induce LDH release.

D. Calculations: for lactate
1. Lactate OD-bkg: raw OD values—115 mM NaCl HB background.
2. Lactate µM: lactate calculation extrapolated from the lactate standard curve. Note that unlike the LDH calculation, the lactate concentration stated is the concentration within the cuvette.
3. Dilution factor: above except will be multiplied by 0.01 for below calculation.
4. Total lactate nmol: lactate µM multiplied by 4.8 (since 50 µl sample in 240 µl assay)=µM in actual sample. This value is multiplied by 5 ml=total nmol lactate in 5 ml. The total nmol lactate is then multiplied by the dilution factor above.

Cells Used in Assays and Their Preparation for the Assays

Cells are maintained in Cassio modified HAM F-12 medium supplemented with 33 mM sodium bicarbonate, 50 µg/ml streptomycin, 200 Unit/ml penicillin G, 0.5 µg/ml amphotericin B, 10 mM sodium hypoxanthine, 40 µM aminopterin, and 1.6 mM thymidine (HAT), and 5% fetal bovine serum. The WIF-B cells are derived from a fusion of a HGPRTase$^-$ rat hepatoma cell (FAO) and a normal human lung fibroblast (WI-38). The fibroblasts confer the ability of the fused cells to grow in the presence of HAT. The cells are kept at 37° C. in a humidified incubator with 7% CO$_2$ atmosphere. Cells are grown on plastic tissue culture flask or on glass coverslips. The medium was replaced every other day to day 7, then changed daily thereafter.

Subculturing was performed by dislodging cells from the flask by treatment with a solution containing 0.05% trypsin, 0.5 mM EDTA, 137 mM NaCl, 5.4 mM KCl, and 0.058% NaHCO$_3$. Following harvesting, WIF-B cells were seeded onto plastic flasks or glass coverslips at a density of 1–2×10$^4$ cells/cm$^2$. Cells used for carrying the cell line were grown to a density between 1–1.5×10$^5$/cm$^2$ in about 7 days. For assays, cells were grown to higher densities and used 9–11 days post seeding.

Various compounds were tested as set forth in the following table. To the extent feasible, the groups of compounds were classified according to a potential mechanism by which the compounds may be active.

TABLE

| Class | Action | Example |
|---|---|---|
| Class-1 | decrease redox stress | purine-ribonucleoside |
| Class-2 | receptor | purine-ribonucleotide |
| Class-3 | receptor | ribulose bis 1,5-PO4 |
| Class-4 | ATP supplement | fructose |
| Class-5 | redox-sink | pyruvate, acetoacetate |
| Class-6 | endogenous protect | Vit-E, glutathione |
| Class-7 | — | amino acids, glycine, alanine |
| Class-8 | — | — |
| Class-9 | — | — |
| Class-10 | misc. | nucleotide transport inhibitors, apoptosis inhibitors |

In the following table, Table 1, a number of compounds were tested in the LDH assay and their activity compared to the activity of guanosine in reducing the proportion of extracellular LDH as compared to total LDH after contact of the cells with an inhibitor. Based on their chemical structure and/or mode of action, the various compounds were collected together in classes for comparison.

TABLE 1

| compound | activity (% of guanosine) | maximum effective concentration |
|---|---|---|
| Class-1 | | |
| guanosine | 100 | 500 µM |
| Adenosine | 85 | 500 µM |
| Inosine | 90 | 500 µM |
| 6-mercaptopurine riboside | 90 | 500 µM |
| N6-cyclopentyladenosine | 20 | 500 µM |
| 2'deoxyadenosine | 70 | 500 µM |
| Xanthosine | 10 | 500 µM |
| Benzoyl adenosine | 10 | 500 µM |
| 1-methylinosine | 20 | 500 µM |
| 5'deoxy 5' methylthioadenosine | 10 | 500 µM |
| 6-dimethylallylamino purine riboside | 10 | 500 µM |
| 5' amino 5'deoxyadenosine | 10 | 500 µM |
| Adenosine periodate | 10 | 500 µM |
| Adenosine 5' monosulfate | 40 | 500 µM |
| 7-methylinosine | 40 | 500 µM |
| alpha-adenosine | 10 | 500 µM |
| 6-Cl purine riboside | 30 | 500 µM |
| 5'Cl-5'deoxyadenosine | 5 | 500 µM |
| 2'deoxyinosine | 30 | 500 µM |
| 2'deoxyguanosine | 40 | 500 µM |
| 2,6 diaminopurine 2'deoxy riboside | 70 | 500 µM |
| 5'deoxyadenosine | 30 | 500 µM |
| 5-Iodotubercidin | 50 | 500 µM |
| 6-mercaptopurine | 5 | 500 µM |
| 6-mercaptoguanosine | 70 | 500 µM |
| 2-amino 6-Cl-purine riboside | 40 | 500 µM |
| N2-methylguanosine | 50 | 500 µM |
| 5'-S-isobutyladenosine | 50 | 500 µM |
| Adenosine 5'succinate | 10 | 500 µM |
| 2'3' DiO acetyl adenosine | 40 | 500 µM |
| 6-hydroxyguanidine purine riboside | 2 | 500 µM |
| 2-Phenylaminoadenosine | 70 | 500 µM |
| 5-Iodoadenosine | 5 | 500 µM |
| 2'-Omethyladenosine | 10 | 500 µM |
| S-(2hydroxy 5-nitrobenzyl) 6-thioinosine * | 150 | 100 µM |
| Class-2 | | |
| ADP | 80 | 500 µM |
| ATP | 75 | 500 µM |
| AMP | 85 | 500 µM |

TABLE 1-continued

| compound | activity (% of guanosine) | maximum effective concentration |
|---|---|---|
| 3' AMP | 60 | 20 mM |
| IMP | 85 | 500 µM |
| Cordycepin | 60 | 20 µM |
| 2'deoxy-IMP | 70 | 500 µM |
| 2'deoxy-AMP | 70 | 500 µM |
| N2,2'0-dibutyrlguanosine3'5'cyclic monophosphate | 4 | 500 µM |
| N2,2'0-dibutyrladenosine3'5'cyclic monophosphate | 2 | 500 µM |
| NAD | 50 | 500 µM |
| 2'deoxy-GMP | 70 | 500 µM |
| Class-3 | | |
| 3'5' adenosine diphosphate (3'5'PAP) | 60 | 20 mM |
| Ribulose 1,5 Diphosphate | 65 | 20 mM |
| Glucose 1,6 Diphosphate | 5 | 20 mM |
| Fructose 2,6 Diphosphate | 30 | 20 mM |
| 2'5' adenosine diphosphate (2'5'PAP) | 10 | 20 mM |
| Adenosine 5'diphosphoribose (ADP-ribose) | 50 | 800 µM |
| Class-4 | | |
| Fructose | 50 | 30 mM |
| 3-phosphoglycerate | 5 | 10 mM |
| Glucose | 20 | 30 mM |
| Fructose 1,6 Diphosphate | 20 | 30 mM |
| Fructose-6-phosphate | 10 | 30 mM |
| Mannose | 20 | 30 mM |
| Class-5 | | |
| Pyruvate | 30 | 20 mM |
| Phenylalanine | 30 | 30 mM |
| alpha-Ketoglutarate | 5 | 20 mM |
| malate | 5 | 20 mM |
| Acetoacetate | 10 | 20 mM |
| Class-6 | | |
| Arginine | 60 | 30 mM |
| Glutamate | 20 | 30 mM |
| Glutathione (oxidized) | 20 | 20 mM |
| N,N-dimethylglycine | 10 | 20 mM |
| Glycine amide | 110 | 20 mM |
| Glycine methyl ester | 120 | 20 mM |
| Alanine methyl ester | 120 | 2 mM |
| Class-7 | | |
| alanine | 100 | 5 mM |
| Glycine | 100 | 5 mM |
| Serine | 10 | 30 mM |
| Glutamate | 20 | 30 mM |
| Tryptophan | 60 | 30 mM |
| Glutamine | 60 | 30 mM |
| Lysine | 5 | 1 mM |
| Sarcosine | 100 | 5 mM |
| Class-10 | | |
| Aurintricarboxylic acid | 10 | 10 µM |
| Taurine | 20 | 30 mM |
| cytosine | 30 | 500 µM |
| Thymidine | 30 | 500 µM |
| Theophylline | 4 | 500 µM |
| Orotate | 10 | 500 µM |
| Cycloserine | 40 | 20 mM |
| Methylene Blue | 60 | 40 µM |
| S-4 Nitrobenzyl 6-thioinosine (NBTI) | 60 | 500 µM |
| erythro-9-(2-hydroxy-3-nonyl)adenine EHNA | 95 | 500 µM |
| Mycophenolic Acid | 50 | 500 µM |

* = not based on maximum effective concentration

In addition, following the above procedures, combinations of compounds were employed.

TABLE 2

| | % LDH Release | | | |
|---|---|---|---|---|
| Time, hour | Nothing | Guanosine, 500 μM | Guanosine, 500 μM; Pyruvate, 1 mM | Guanosine, 500 μM; Pyruvate, 1 mM; Glycine, 1 mM |
| 2 | 50 | 0 | 0 | 0 |
| 4 | 70 | 10 | 5 | 0 |
| 7 |  | 25 | 25 | 5 |
| 9 | 90 | 60 | 60 | 10 |

In the next study, protection as a result of adding guanosine at 500 μM was determined by performing the LDH release analysis where the guanosine was added at different times after 100 μM antimycin A was added, followed by determination of the LDH release over the next two hours. The following table indicates the results.

TABLE 3

| | % LDH Release | |
|---|---|---|
| Time delay, hour | Nothing | Guanosine, 500 μM |
| 0 | 65 | 4 |
| 0.5 | 89 | 8 |
| 1 | 91 | 24 |
| 1.5 | 93 | 46 |
| 2 | 103 | 75 |

It is evident from the above results that administering the guanosine to the cells as long as 1.5 hours after the stress has been initiated still provides a significant degree of protection.

The above data demonstrates that by employing a variety of purines to cells under stress, either by themselves or in conjunction with other compounds, including compounds which have been known or not known to provide for protection against stress, the time to irreversible changes leading to cellular mortality can be greatly extended. The results demonstrate that there is substantial improvement available, including compounds which are generally regarded as safe and can be used in relatively high concentrations, by themselves, or in combination with other substances. These compositions can provide extensive opportunities in a variety of situations involving in vitro, ex vivo and in vivo situations. Thus, cells and organs may be stably maintained for extended periods of time, even under such stresses as cryogenic preservation and reoxygenation upon thawing. The subject compositions may also be used in vivo, by administering systemically or locally in situations where hypoxia may be anticipated or has occurred.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for delaying the time that mammalian cells under stress due to energetic dysfunction undergo irreversible change related to said stress, said method comprising:
    adding to a medium comprising said cells in an amount sufficient to delay the time for said irreversible change at least one of an electron acceptor and an amino acid and a purine derivative other than adenosine triphosphate or adenosine.

2. A method according to claim 1, wherein said stress is hypoxia.

3. A method according to claim 2, wherein said purine derivative is an $N^9$-ribosylated purine.

4. A method according to claim 3, wherein said $N^9$-ribosylated purine is guanosine or inosine.

5. A method according to claim 3, wherein said $N^9$-ribosylated purine is 6-mercaptopurine riboside.

6. A method according to claim 1, wherein both an electron acceptor and an amino acid are added.

7. A method of inhibiting the effects of hypoxia in a cell or tissue culture, said method comprising:
    adding to said culture in an amount sufficient to delay the time for cells in said cell culture to undergo irreversible changes related to said hypoxia an $N^9$-ribosylated purine.

8. A method according to claim 7, wherein said $N^9$-ribosylated purine is guanosine, inosine or 6-mercaptopurine riboside.

9. A method of inhibiting the effects of hypoxia in a mammalian host, said method comprising:
    adding to said host in an amount sufficient to delay the time for cells in said host to undergo irreversible changes related to said hypoxia an $N^9$-ribosylated purine other than adenosine.

10. A method according to claim 9, wherein said $N^9$-ribosylated purine is guanosine inosine or 6-mercaptopurine riboside.

11. A composition comprising a concentrate capable of forming a solution of a purine derivative in combination with at least one of an electron acceptor and an amino acid, wherein said solution comprises said purine derivative at a concentration in the range of about 0.1 μM to 5 mM and said electron acceptor and/or amino acid are in a molar ratio of 1:1–100 to said purine derivative.

12. A composition according to claim 11, wherein said electron acceptor is an α- or β-ketocarboxylic acid and said amino acid is a naturally occurring amino acid of from 2 to 3 carbon atoms.

13. A composition according to claim 12, wherein said purine derivative is guanosine, said α-ketocarboxylic acid is pyruvate and said amino acid is glycine.

14. A cellular composition comprising dispersed cells, tissue or viable organ and in an amount sufficient to delay the time for occurrence of an irreversible change in said cells, tissue or viable organ leading to mortality, a purine derivative other than a triphosphate.

15. A cellular composition according to claim 14, wherein said purine derivative is an $N^9$-ribosylated purine and further comprising at least one of an electron acceptor and amino acid in a molar ratio of 1:1–100 to said purine derivative.

16. In a method for transplanting cells or an organ, where said cells or organ are maintained for a period of time between isolation and implantation, the improvement which comprises:

storing said cells or organ during said period of time in a composition comprising an $N^9$-ribosylated purine.

17. A composition comprising a concentrate capable of forming a solution of a purine derivative in combination with at least one of an electron acceptor and an amino acid, wherein said solution comprises said purine derivative at a concentration in the range of about 0.1 µM to 5 mM and said electron acceptor and/or amino acid are in a molar ratio of 1:1–100 to said purine derivative, wherein the purine derivative is guanosine.

18. A cellular composition comprising dispersed cells, tissue or viable organ and in an amount sufficient to delay the time for occurrence of an irreversible change in said cells, tissue or viable organ leading to mortality, a purine derivative other than a triphosphate or adenosine.

19. In a method for transplanting cells or an organ, where said cells or organ are maintained for a period of time between isolation and implantation, the improvement which comprises:

storing said cells or organ during said period of time in a composition comprising guanosine.

20. The method of claim 19, further comprising at least one of an electron acceptor and an amino acid.

* * * * *

UNITED STATES PATENT AND TRADEMARK OFFICE
CERTIFICATE OF CORRECTION

PATENT NO. : 5,801,159
DATED : September 1, 1998
INVENTOR(S) : MILLER et al.

It is certified that error appears in the above-indentified patent and that said Letters Patent is hereby corrected as shown below:

Column 7, line 17, insert --.-- after the word "release".

Column 7, line 61, insert --:-- after the word "Calculations".

Column 7, line 66, change "not" to read --not--.

Column 8, line 55, reads "at 37° C." and should read --at 37° C--.

Column 10, line 61, insert the paragraph "Activity of each compound is expressed as % of the lead compound guanosine (guanosine at 100%) at the compound's maximal effective concentration".

Signed and Sealed this

Second Day of March, 1999

Attest:

Q. TODD DICKINSON

*Attesting Officer*  *Acting Commissioner of Patents and Trademarks*